(12) United States Patent
Akitomi

(10) Patent No.: US 8,370,069 B2
(45) Date of Patent: Feb. 5, 2013

(54) METHOD FOR PREDICTING SECONDARY STRUCTURE OF NUCLEIC ACID SEQUENCE, A PREDICTOR FOR SECONDARY STRUCTURE OF NUCLEIC ACID SEQUENCE AND A PREDICTING PROGRAM FOR PREDICTING SECONDARY STRUCTURE OF NUCLEIC ACID SEQUENCE

(75) Inventor: Jou Akitomi, Tokyo (JP)

(73) Assignee: NEC Soft, Ltd., Tokyo (JP)

( * ) Notice: Subject to any disclaimer, the term of this patent is extended or adjusted under 35 U.S.C. 154(b) by 1295 days.

(21) Appl. No.: 12/124,467

(22) Filed: May 21, 2008

(65) Prior Publication Data

US 2008/0294351 A1    Nov. 27, 2008

(30) Foreign Application Priority Data

May 21, 2007    (JP) ................................. 2007-134529

(51) Int. Cl.
*G06F 7/00*    (2006.01)
(52) U.S. Cl. ............ 702/19; 703/11; 707/700; 536/23.5
(58) Field of Classification Search ........................ None
See application file for complete search history.

(56) References Cited

PUBLICATIONS

Akito Taneda, "Prediction of Pseudoknotted RNA Structure by a Structural Alignment Using GeneticAlgorithm" Genome Informatics 2005, Poster Abstract: P126, 16th International Conference on Genome Informatics, Dec. 19-21, 2005, Yokohama Pacifico, Japan.
Kouichi Okada et al., "Predicting Non-Coding RNAs Based on Free Energy Minimization by Means of Genetic Algorithms" Genome Informatics 2005, Poster Abstract: P136, 16th International Conference on Genome Informatics, Dec. 19-21, 2005, Yokohama Pacifico, Japan.
Stefan Washietl, "Prediction of Structural non-Coding RNAs by Comparative Sequence Analysis", Thesis, Oct. 2005, University of Vienna.
Karklin, et al., "Classification of Non-Coding RNA Using Graph Representations of Secondary Structure", Pacific Symposium on Biocomputing, 2005, pp. 4-15, vol. 10.
Sakakibara, et al., "Sequence and Structural Analyses for Functional Non-Coding RNAs", Journal of Japanese Society for Artificial Intelligence, 2007, pp. 54-62, vol. 22.
Kin, et al., "Marginalized Kernels for RNA Sequence Data Analysis", Genome Informatics, 2002, pp. 112-122.
Gorodkin et al., Nucleic Acids Research, 1997. vol. 25, p. 3724-3732.
Pavesi et al. "RNA Profile: an algorithm for finding conserved secondary structure motifs in unaligned RNA sequences", Nucleic Acid Research, 2004, vol. 32, No. 10 pp. 3258-3269.
Macke et al. "RNAMotif, and RNA secondary structure definition and search algorithm", Nucleic Acids Research, 2001, vol. 29, No. 22, pp. 4724-4735.
Kjems et al. "Secondary Structural Elements Exclusive to the Sequences Flanking Ribosomal RNAs Lend Support to the Monophyletic Nature of the Archaebacteria", Journal of Molecular Evolution, 1990, vol. 31, No. 1, pp. 25-32.

*Primary Examiner* — Mary Zeman
(74) *Attorney, Agent, or Firm* — Sughrue Mion, PLLC

(57) ABSTRACT

An exemplary object of the present invention is to provide method, predictor and predicting program for predicting secondary structure of nucleic acid sequence capable of evaluating not only overall similarity and but also localized similarity of secondary structure of nucleic acid sequence. A method according to an exemplary aspect of the present invention includes the steps of:
  extracting a structural element of the secondary structure from the secondary structure of the nucleic acid sequence; and
  evaluating a similarity of each structural element of the nucleic acid sequence as a subject, based on a feature vector of the structural element.

33 Claims, 5 Drawing Sheets

FIG. 5

```
Sequence 1:   AAACCCGAAAGGGUUUUGAGAAAAA
Structure 1:  :::((((::::)))::(((((::::))))
                  ------------------   ----------------------
                       Stem 1-1              Stem 1-2

Sequence 2:   CCCCCGAGAGGGGUUUUGCCCUUGCC
Structure 2:  :((((::::))))::::((((::::))):
              ------------------------   ----------------
                     Stem 2-1              Stem 2-2
```

METHOD FOR PREDICTING SECONDARY STRUCTURE OF NUCLEIC ACID SEQUENCE, A PREDICTOR FOR SECONDARY STRUCTURE OF NUCLEIC ACID SEQUENCE AND A PREDICTING PROGRAM FOR PREDICTING SECONDARY STRUCTURE OF NUCLEIC ACID SEQUENCE

RELATED APPLICATION

The present invention is based upon and claims the benefit of priority from Japanese patent application No. 2007-134529, filed on May 21, 2007, the disclosure of which is incorporated herein in its entirety by reference thereto.

FIELD OF THE INVENTION

The present invention relates to a method for predicting secondary structure of nucleic acid sequence, and a predictor for secondary structure of nucleic acid sequence and predicting program for predicting secondary structure of nucleic acid sequence for carrying out the method.

BACKGROUND OF THE INVENTION

Nucleic acid sequences such as DNA and RNA are molecules consisting of four types of bases of adenine (A), cytosine (C), guanine (G) and thymine (T) or uridine (U). It is known that the function of the molecule of the nucleic acid sequence is dependent on the secondary structure of the sequence. The dependency is a nature which is exerted not only by a functional nucleic acid typified by so-called structural gene such as exon, but also by non-structural gene such as intron and by various types of nucleic acid sequence which cannot be internally transcribed in the cell based on the central dogma such as aptamer.

Although the prediction of the secondary structure of the nucleic acid sequence is very important, different structures may be obtained even if the same sequences have each other, and identical or similar structures may be obtained even if the different sequences have each other. In the case that the secondary structure of the nucleic acid sequence has been merely predicted, it can be largely considered that such a structure will not necessarily provide a possibly-suitable secondary structure in such a sequence. Indeed, with regard to an authentically-synthesized nucleic acid sequence such as so-called aptamer, the biological functions are often exerted only from a specific important region of the nucleic acid sequence. It is expected that such specific region(s) has the structural similarity, however, the structural similarities with regard to the other region(s) do not always have each other. Many attempts have been made to improve the accuracy for predicting the secondary structure of the nucleic acid sequence in that a similarity of each secondary structures of the specific nucleic acid sequence is evaluated with the secondary structure of the other nucleic acid sequence.

Examples of the similarity comparison method of the secondary structure of the nucleic acid sequence generally include a method for an evaluation by combining the alignment of the base constituting the nucleic acid sequence with the prediction of the secondary structure of the nucleic acid sequence. In addition, several algorithms have been reported that probabilities for forming base pairs in the nucleic acid sequence is originally estimated, and, based on the probabilities, predicted structure(s) are modified and re-constituted into the actual structure (non-patent related document 1).

However, in the case of evaluating the similarity of the secondary structure of the nucleic acid sequence with such a method, the similarity as overall structure will be basically predicted. Therefore, it is difficult to precisely predict the similarity of the target structure of a nucleic acid sequence which can be taken in the similar structure in localized region not in overall structure.

Non-Patent Related Document 1

Gorodkin et al., Nucleic Acids Research, 1997, vol. 25, p. 3724–3732

SUMMARY OF THE DISCLOSURE

The present invention is aimed to propose in accordance with such a problem, and is to provide a method for predicting secondary structure of nucleic acid sequence capable of evaluating not only overall similarity and but also localized similarity of secondary structure of nucleic acid sequence, and a predictor for secondary structure of nucleic acid sequence and a predicting program for carrying out said method.

A method for predicting secondary structure of nucleic acid sequence according to the present invention is characterized in that:

A method for predicting secondary structure of nucleic acid sequence comprising the steps of:

extracting a structural element of the secondary structure from the secondary structure of the nucleic acid sequence; and evaluating a similarity of each structural element of the nucleic acid sequence as a subject, based on a feature vector of the structural element.

A predictor for secondary structure of nucleic acid sequence according to the present invention is characterized in that:

A predictor for secondary structure of nucleic acid sequence comprising:

an extractor of structural element nucleic acid sequence for extracting a structural element of the secondary structure from the structural element of the nucleic acid sequence; and a localized structural similarity evaluator for evaluating a similarity of each structural element of the nucleic acid sequence as a subject, based on a feature vector of the structural element.

A predicting program for predicting secondary structure of nucleic acid sequence according to the present invention is characterized in that:

A predicting program for predicting secondary structure of nucleic acid sequence executing the steps of:

extracting a structural element of the secondary structure from the secondary structure of the nucleic acid sequence; and evaluating a similarity of each structural element of the nucleic acid sequence as a subject, based on a feature vector of the structural element.

An exemplary advantage according to the invention is capable of evaluating the similarity between the structures of the sequences in an arbitrary window size even in the localized or overall structure.

In addition, it is possible to precisely predict the secondary structure by using several sequences for inputting, rather than single sequence, since the nucleic acid sequences having the same functions has generally the similar structures.

Further, it is more likely to be an important region for the function of the nucleic acid in the case of being found a localized similar portion of the locally similar structure.

Therefore, according to the present invention, it is possible to predict the functionally-important region in the nucleic acid sequence.

Other features and advantages of the present invention will be apparent from the following description taken in conjunction with the accompanying drawings, in which like reference characters designate the same or similar parts throughout the figures thereof.

BRIEF DESCRIPTION OF THE DRAWING

FIG. 5 discloses 1 and 2 (i.e., SEQ ID NOs: 1 and 2, respectively) and structures used in Exemplary embodiment 1.

BEST MODE FOR CARRYING OUT THE INVENTION

The present invention relates to a method for examining a similarity of a secondary structure of a nucleic acid sequence along with minimizing the effect on the type of the structures contained in the nucleic acid sequence, in which elements of each structure as obtained in predicting the secondary structure of the nucleic acid sequence are extracted to express as a vector indicating a characteristic of the element, and a correlation between the vector originated from the secondary structure of the nucleic acid sequence as a subject and the vector originated from the secondary structure of the nucleic acid sequence as reference is estimated.

Hereinafter, it will be given the detailed explanation of the method for predicting secondary structure of nucleic acid sequence, the predictor for secondary structure of nucleic acid sequence and the predicting program for predicting secondary structure of nucleic acid sequence according to the present invention with reference to the accompanying drawing.

It should be noted that the predictor for secondary structure of nucleic acid sequence according to the present invention is an apparatus for executing the method for predicting secondary structure of nucleic acid sequence according to the present invention and that the predicting program for predicting secondary structure of nucleic acid sequence according to the present invention is a program for executing the method for predicting secondary structure of nucleic acid sequence according to the present invention. In addition, in the present invention, the nucleic acid sequence refers to several types of gene sequence such as DNA and RNA.

Figure 1:
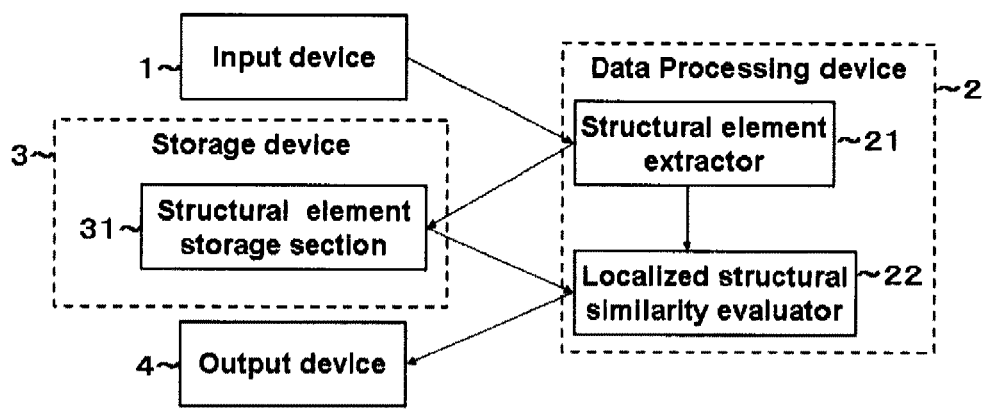
FIG. 1 is a schematic diagram of predictor for secondary structure of nucleic acid sequence according to the present invention.

FIG. 1 shows the schematic diagram of predictor for secondary structure of nucleic acid sequence according to the present invention. The predictor for secondary structure of nucleic acid sequence according to the present invention comprises an input device 1 such as the keyboard, a data processing device 2 operating based on the program control, a storage device 3 storing the information and an output device 4 such as the display apparatus and the printer.

The data processing device 2 comprises an extractor of structural element 21 and a localized structural similarity evaluator 22.

First, the extractor of structural element 21 divides each structure of a candidate structure of the secondary structure of the nucleic acid sequence into a stem structure and a marginal structure with reference to the secondary structure of the nucleic acid sequence as a subject and to the information of the candidate structure wherein the marginal structure is constituted from bases other than the bases constituting the stem structure, thereby extracting structural elements of the stem structure and the marginal structure. Next, the extractor of structural element 21 numerically converts the structural element into a feature vector. The feature vector possesses a characteristic of the numerically-converted structural element in the form of the parallel vector. The structural information of the nucleic acid sequence possessed as set of the feature vector is stored in a structural element storage device 31.

The localized structural similarity evaluator 22 retrieves the information of the candidate structure of the nucleic acid sequence possessed as set of the feature vector (s) stored in the structural element storage device 31, and evaluates a similarity between each feature vector of one nucleic acid sequence and each feature vector of the other nucleic acid sequence. Thereby, the localized similarity of the structure of the nucleic acid sequence as a subject can be evaluated. Each nucleic acid sequence has several information of the candidate structure and several feature vectors of each candidate structure. Therefore, the evaluation of the localized similarity of the structure of the nucleic acid sequence is determined by, for example, evaluating the similarity of the feature vectors possessed in each nucleic acid sequence in the round-robin fashion.

The feature vector originated from the stem structure and marginal structure as divided from one candidate structure may be used as the subject in the localized structural similarity evaluator 22 for evaluating the similarity with reference to the feature vector stored in the structural element storage device 31. Alternatively, a combination of each feature vector originated from one stem structure and one marginal structure present around this stem structure may be used as the subject for evaluating the similarity. Note that examples of a method of combining the feature vectors include the well-known arithmetic method such as addition, subtraction, multiplication and division of the vector.

In the case of using each feature vector in combination, the nucleic acid sequence is divided into a stem-loop unit based on one candidate structure, and is handled as set of stem-loop unit(s). That is, in the case of existing several candidate structures in one nucleic acid sequence, there will be set of several stem-loop units in one nucleic acid sequence. In addition, the stem-loop as unit possesses the information in the form of the feature vector depending on the structural element.

In addition, examples of the evaluation of the similarity of the feature vector which may be used in the localized structural similarity evaluator 22 are not limited so far as the method can evaluate the correlation of vector. Among them, examples of the evaluation include the inner product used in the correlational analysis of vector, and pattern classification algorithms such as support vector machine (SVM).

The storage device 3 comprises the structural element storage device 31.

The structural element storage device 31 storages the information of the feature vector of the nucleic acid sequence extracted by the extractor of structural element 21. Examples of parameters contained in the feature vector are not limited so far as the parameter presents a characteristic of the structural element, and includes type and number of the base constituting the structural element, the free energy which can be made in the structural element, and type of the structure such as the stem structure and the loop structure.

<Steps of the Method for Predicting Secondary Structure of Nucleic Acid Sequence According to the Present Invention, and Operation of the Predictor for Secondary Structure of Nucleic Acid Sequence and Predicting Program for Predicting Secondary Structure of Nucleic Acid Sequence According to the Present Invention, and the Others>

Next, it will be given the detailed explanation of the steps of the method for predicting secondary structure of nucleic acid sequence according to the present invention, and operation of the predictor for secondary structure of nucleic acid sequence and predicting program for predicting secondary structure of nucleic acid sequence according to the present invention, and the others with reference to the schematic diagram of FIG. 1, and the flowcharts of FIGS. 2 to 4.

Figure 2:
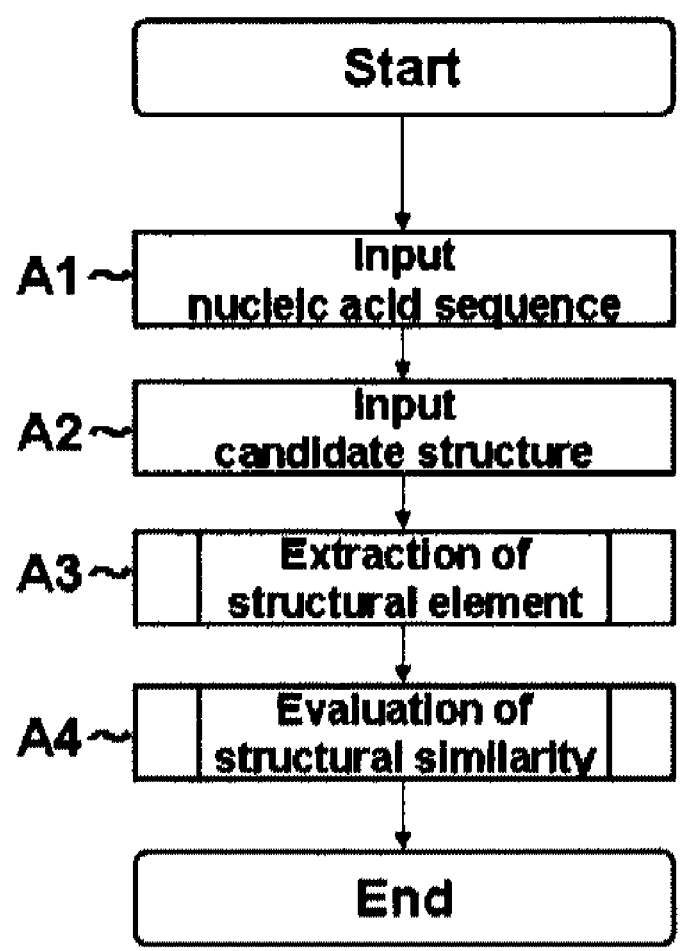
FIG. 2 is a flowchart showing the steps of the method for predicting secondary structure of nucleic acid sequence according to the present invention.
Figure 3:
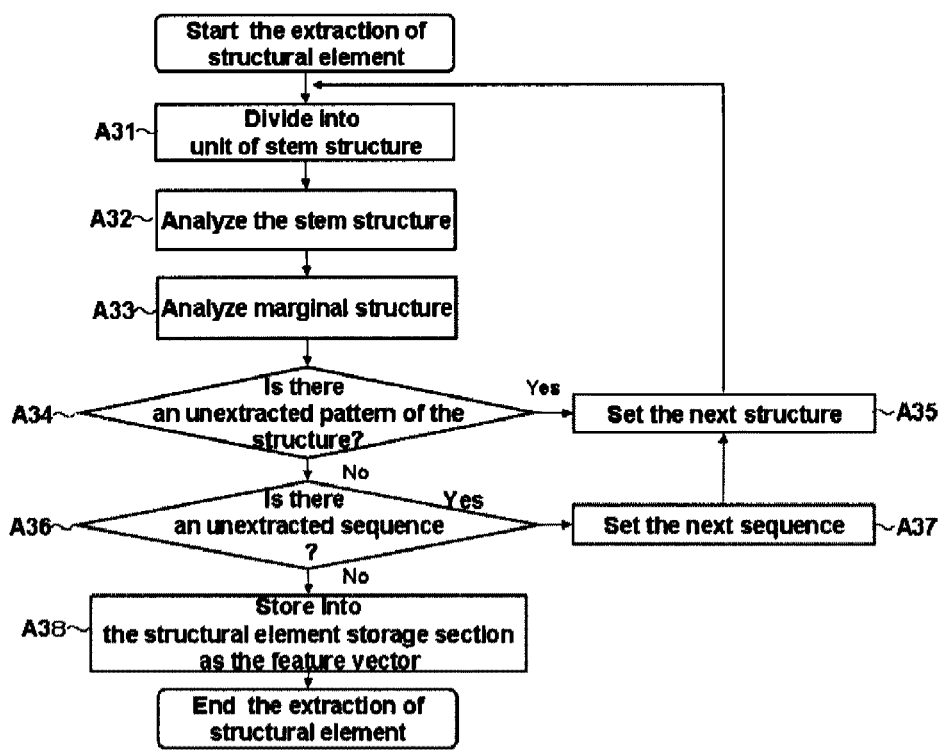
FIG. 3 is a flowchart showing the step of extracting the structural element.
Figure 4:
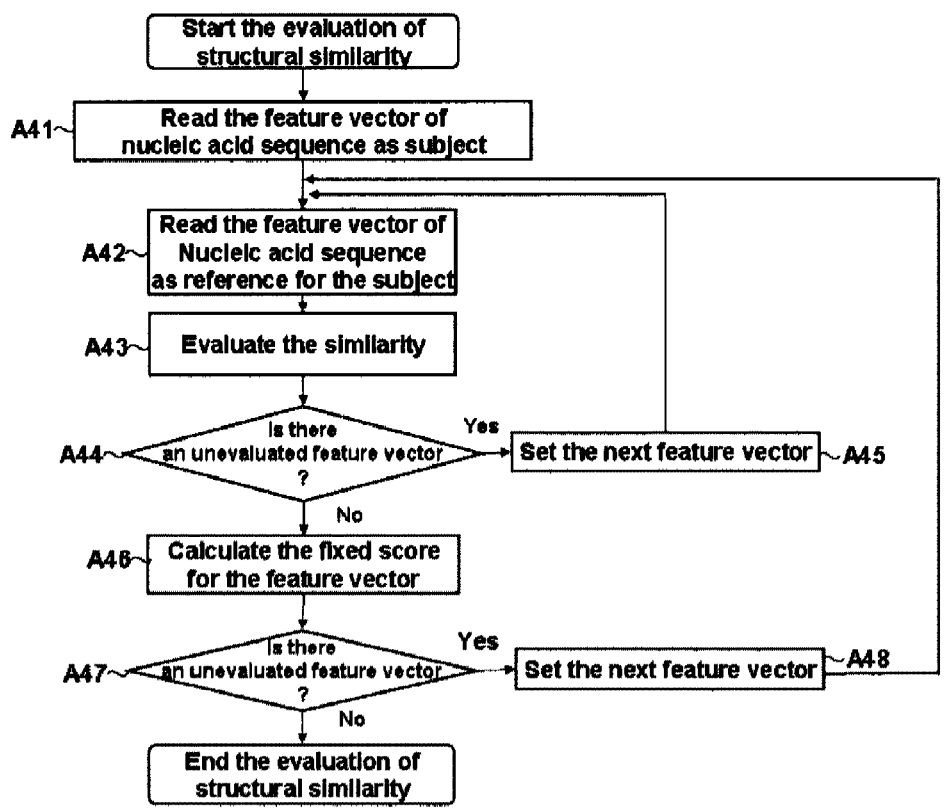
FIG. 4 is a flowchart showing the step of evaluating the structural similarity based on the feature vector of each structure.

Note that FIG. 2 is the flowchart showing the steps of the method for predicting secondary structure of nucleic acid sequence according to the present invention, FIG. 3 is the flowchart showing the step of extracting the structural element and FIG. 4 is the flowchart showing the step of evaluating the structural similarity based on the feature vector of each structure.

In the predictor for secondary structure of nucleic acid sequence according to the present invention, the nucleic acid sequence and the information of the candidate structure of the nucleic acid sequence, given from the input device 1, are transferred to the extractor of structural element 21 (A1, A2, A3). The candidate structure of the secondary structure of the nucleic acid sequence may be input as shown in step A2, or the candidate structure of the secondary structure may be obtained from a well-known predicting means capable of predicting the secondary structure of the nucleic acid sequence, wherein the predicting means are contained in the predictor for secondary structure of nucleic acid sequence according to the present invention.

The extractor of structural element 21 divides the candidate structure into the unit of the stem structure with reference to the first candidate structure of the first nucleic acid sequence (A31). Next, the extractor of structural element 21 analyzes the stem structure divided from the candidate structure (A32). The analysis of the stem structure is performed in which various elements of the stem structure (in the present invention, referred also to as a structural element of the stem structure) are extracted and each of the structural elements is numerically converted. Examples of the structural element of the stem structure include length of the stem structure, type of base pair constituting the stem structure and an appearance pattern of the base pair. After that, the extractor of structural element 21 performs the analysis as similar to the step A32 that various elements of the marginal structure (in the present invention, referred also to as a structural element of the marginal structure, and these correlatively-referred to as, simply, a structural element) constituting the bases other than the bases constituting the stem structure are extracted as the structural element of the marginal structure, and that each structural element is numerically converted (A33). Examples of the marginal structure are not limited so far as the structure is constituted of bases other than the bases constituting the stem structure, and include the well-known structure as structures for the base sequence, for example, the loop structure such as the bulge loop structure, the inner loop structure, the hairpin loop structure, the multibranched loop structure and the single strand end, and particular kind of the structures such as the pseudoknot and G quartet. In addition, examples of the structural element of the marginal structure include number of the bases constituting the marginal structure, type of the base constituting the marginal structure and an appearance pattern of the base.

So obtained values as numerically converted from each structural element of the stem structure and the marginal structure are possessed in the feature vector as a characteristic of the stem structure and the marginal structure.

Next, the extractor of structural element 21 determines whether there is an unextracted pattern of the structure in the first nucleic acid sequence (A34). In the case of being determined that there is an unextracted pattern of the structure, the structure is set (A35), and each step of the steps A31 to A33 is repeated until there is not an unextracted pattern of the structure in the first nucleic acid sequence. After that, the extractor of structural element 21 determines whether there is a nucleic acid sequence which the feature vector is not extracted (A36). In the case of being determined that there is an unextracted nucleic acid sequence, the sequence is set (A37), and each step of the steps A31 to A35 is repeated until there is not an unextracted nucleic acid sequence. After the extraction the feature vector from the nucleic acid sequence and the candidate structure is finished, these feature vectors are stored in the structural element storage device 31 (A38), and the step of extracting the structural element is finished (A3).

Next, after the step A3 of extracting the structural element is finished, the predictor for secondary structure of nucleic acid sequence according to the present invention performs step A4 of evaluating the similarity of the candidate structure by using the localized structural similarity evaluator 22, based on each feature vector from the stem structure and the marginal structure as obtained in the step A3.

First, the localized structural similarity evaluator 22 reads the information of the feature vector of the nucleic acid sequence as a subject from the structural element storage device 31 (A41). Next, the localized structural similarity evaluator 22 reads the information of the feature vector of the nucleic acid sequence as a reference for the subject (A42). After that, the localized structural similarity evaluator 22 evaluates the similarity between the feature vector as the subject and the feature vector as the reference for the subject to obtain a candidate score of the feature vector as the subject (A43).

Examples of the method for evaluating the similarity of each feature vector include the correlational analysis of vector such as estimation of the inner product of two vectors.

Next, the localized structural similarity evaluator 22 determines whether, among the feature vector as the reference for the subject, there is the feature vector which is not set as the reference for the subject for evaluation of the similarity (A44) In the case of being determined that there is an unevaluated feature vector among the feature vector as the reference for the subject, the localized structural similarity evaluator 22 sets the feature vector as a feature vector as a reference for the subject (A45), and each step of the steps A42 to A43 is repeated until there is not an evaluated feature vector among the feature vector as the reference for the subject. So, with regard to the feature vector as the subject, the candidate score of the feature vector as the subject for all feature vectors as the reference for the subject is obtained. The localized structural similarity evaluator 22 calculates a fixed score as to one feature vector as the subject based on the candidate score (A46). Examples of the fixed score include an average of the candidate scores of the feature vectors having highest similarity for each nucleic acid sequence, and number of feature vectors which are evaluated as having over a predetermined similarity.

Next, the localized structural similarity evaluator 22 determines whether there is an unevaluated feature vector of the nucleic acid sequence as a subject (A47). In the case of being determined that there is an unevaluated feature vector as the subject, the feature vector is set (A48), and each step of the steps A42 to A46 is repeated until there is not the unevaluated feature vector of the nucleic acid sequence as the subject, as mentioned above.

So, the fixed score indicating the similarity for all of the feature vectors is obtained. Accordingly, with regard to one nucleic acid sequence, the feature vector which tends to be often found in the other sequence, that is, the localized similarity of the structures is found. These information of the evaluation result are output to the output device 4 such as the display.

As mentioned above, in the present invention, note that the extractor of structural element 21 has a function of extracting a structural element of the secondary structure from the secondary structure of the nucleic acid sequence, and that the localized structural similarity evaluator 22 has a function of evaluating a similarity of each structural element of the nucleic acid sequence as a subject, based on a feature vector of the structural element.

EXEMPLARY EMBODIMENT

First, as assumed that sequences of Sequence Numbers 1 and 2 (i.e., SEQ ID NOs: 1 and 2, respectively) the structures of the sequences as shown in FIG. 5 are input from the input device 1, these are transferred to the extractor of structural element 21 (A1, A2, A3).

First, the extractor of structural element 21 divides the structure 1 into unit of the stem structure with reference to the structural information of the structure 1 (A31). The structure 1 is divided into two stem structures of stem 1-1 and stem 1-2 in the step (A31). In the case of focusing only on the lengths of the stem and loop with regard to each stem structure, the length of the stem in the stem 1-1 is 3 and the length of the loop in the stem 1-1 is 4. In addition, the length of the stem in the stem 1-2 is 4 and the length of the loop in the stem 1-2 is 4. Next, the extractor of structural element 21 numerically converts characteristics of these structural elements into (3,4) and (4,4), and these are possessed as the feature vector (A32, A33). As an unextracted pattern of the structure, there is not a candidate structure other than the structure 1 in the sequence 1 (A34). In addition, as an unextracted sequence, there is the sequence 2 other than the sequence 1 (A36). Further, there is the structure 2 in the sequence 2. Therefore, the structure 2 of the sequence 2 is set as a subject for extracting the structural element (A37, A35). Next, the extractor of structural element 21, with regard to the structure 2, divides it into two stem structures of stem 2-1 and converts them into (4,4) and (2,4) as the characteristic of the structural elements of the stems 2-1 and 2-2 as similar to the stem structure of the structure 1, and these are possessed as the feature vector (A32, A33). As an unextracted pattern of the sequence, there is not a structure other than the structure 2 in the sequence 2 (A34). As an unextracted sequence, there is not a sequence other than the sequence 2 (A36). Therefore, the extractor of structural element 21 stores four feature vectors of the stems 1-1 to 2-2 into the structural element storage device 31 (A38), and the step of extracting the structural element is finished.

Next, the localized structural similarity evaluator 22 reads four feature vectors stored in the structural element storage device 31 (A41). Next, the localized structural similarity evaluator 22 sets (3,4) which is the feature vector of the stem 1-1 of the structure 1 in the sequence 1 as a first subject, and evaluates the similarity with (4,4) which is the feature vector of the stem 2-1 of a first stem of the structure 2 in the sequence 2 as the feature vector for a reference for the subject (A42, A43). Here, in the case of evaluating the similarity using the inner product of these two vectors as the correlational analysis of vector, the inner product of these two feature vector is estimated as cos θ=0.9898 (A43). As an unevaluated feature vector, there is the stem 2-2, i.e. the other of the stem structure, in the structure 2 of the sequence 2 (A44). Therefore, the localized structural similarity evaluator 22 evaluates the similarity of the stem 1-1 of the stem structure as the subject with (2,4) which is the feature vector of the stem 2-2 as the reference for the subject (A45, A42). Accordingly, as evaluated the similarity of the stem 2-2 similar to the stem 2-1, the inner product of these two vectors is estimated as cos θ=0.9839 (A43).

As an unevaluated feature vector, there is not the other feature vector in the sequence 2 (A44). Therefore, the localized structural similarity evaluator 22 calculates the fixed score based on the candidate scores of "0.9898" and "0.9839" for the stem 1-1 of the structure 1 of the sequence 1 as the subject (A46). Here, in the case of calculating the highest value of the candidate scores as the fixed score, the localized structural similarity evaluator 22 calculates the value of 0.9898 from the values of "0.9898" and "0.9839" as the fixed score (A46), and the step of evaluating the similarity of the stem 1-1 is finished.

There is the stem 1-2 of the feature vector as a subject of the feature vector of the nucleic acid sequence in the sequence 1 (A47). Therefore, the localized structural similarity evaluator 22 sets (4,4) of the feature vector of the stem 1-2 as the subject of the feature vector of the nucleic acid sequence (A48), and evaluates the similarity with each stem of the sequence 2 as references for the subject as similar to the steps A42 to A45. So, as the result of the similarity of the stem 1-2 with the stems 2-1 and 2-2, the inner product of 1.0 of the feature vector as the fixed score of the stem 1-2 is obtained (A46).

Hereinafter, with regard to the stems 2-1 and 2-2 of the structure 2 in the sequence 2, the evaluation is also performed, the step of evaluating the similarity of the structure is finished when the fixed scores for all of the feature vector are obtained (A47). In the case of the present embodiment, highest values of 1.0 are obtained for the stem 1-2 of the structure 1 in the sequence 1 and the stem 2-1 of the structure 2 in the sequence 2, respectively. Therefore, the localized structural similarity evaluator 22 predicts that the structures of each stem in each sequence have high localized similarity each other.

These evaluation results are output to the output device 4 such as the display if necessary (A4), and the prediction of the sequences 1 and 2 is finished.

In the method for predicting secondary structure of nucleic acid sequence according to the present invention, the step of extracting the structural element may comprise a step of dividing into a stem structure and a marginal structure in the secondary structure of the nucleic acid sequence.

In the method for predicting secondary structure of nucleic acid sequence according to the present invention, the step of extracting the structural element may comprise a step of numerically converting the structural element to obtain the feature vector.

In the method for predicting secondary structure of nucleic acid sequence according to the present invention, the step of evaluating the similarity may comprise a step of evaluating the similarity between the feature vector of the structural element of the nucleic acid sequence as a subject and the feature vector of the structural element of the nucleic acid sequence as a reference for the subject.

In the method for predicting secondary structure of nucleic acid sequence according to the present invention, the step of evaluating the similarity may be performed by using the correlational analysis of vector.

In the method for predicting secondary structure of nucleic acid sequence according to the present invention, the step of evaluating the similarity may comprise a step of obtaining a candidate score of the feature vector as the subject.

In the method for predicting secondary structure of nucleic acid sequence according to the present invention, the step of evaluating the similarity may comprise a step of obtaining a fixed score of the feature vector as the subject.

In addition, in the predictor for secondary structure of nucleic acid sequence according to the present invention, the extractor of structural element may divide the secondary structure into a stem structure and a marginal structure in the secondary structure of the nucleic acid sequence.

In the predictor for secondary structure of nucleic acid sequence, the extractor of structural element may numerically convert the structural element to obtain the feature vector.

In the predictor for secondary structure of nucleic acid sequence, the localized structural similarity evaluator may evaluate the similarity between the feature vector of the structural element of the nucleic acid sequence as a subject and the feature vector of the structural element of the nucleic acid sequence as a reference for the subject.

In the predictor for secondary structure of nucleic acid sequence, the localized structural similarity evaluator may perform the correlational analysis of vector.

In the predictor for secondary structure of nucleic acid sequence, the localized structural similarity evaluator may obtain a candidate score of the feature vector as the subject.

In the predictor for secondary structure of nucleic acid sequence, the localized structural similarity evaluator may obtain a fixed score of the feature vector as the subject.

Further, in the predicting program for predicting secondary structure of nucleic acid sequence according to the present invention, the step of extracting the structural element may comprise a step of dividing into a stem structure and a marginal structure in the secondary structure of the nucleic acid sequence.

In the predicting program for predicting secondary structure of nucleic acid sequence, the step of extracting the structural element may comprise a step of numerically converting the structural element to obtain the feature vector.

In the predicting program for predicting secondary structure of nucleic acid sequence, the step of evaluating the similarity may comprise a step of evaluating the similarity between the feature vector of the structural element of the nucleic acid sequence as a subject and the feature vector of the structural element of the nucleic acid sequence as a reference for the subject.

In the predicting program for predicting secondary structure of nucleic acid sequence, the step of evaluating the similarity may be performed by using the correlational analysis of vector.

In the predicting program for predicting secondary structure of nucleic acid sequence, the step of evaluating the similarity may comprise a step of obtaining a candidate score of the feature vector as the subject.

In the predicting program for predicting secondary structure of nucleic acid sequence, the step of evaluating the similarity may comprise a step of obtaining a fixed score of the feature vector as the subject.

While the invention has been particularly shown and described with reference to exemplary embodiments thereof, the invention is not limited to these embodiments. It will be understood by those of ordinary skill in the art that various changes in form and details may be made therein without departing from the spirit and scope of the present invention as defined by the claims.

What is claimed is:

1. A method for predicting secondary structures within a nucleic acid, comprising:
    (a) a structural element extracting step, comprising extracting data on structural elements of candidate secondary structures from a subject nucleic acid sequence and from a reference nucleic acid sequence; and
    (b) a localized structural similarity evaluating step, comprising evaluating the structural similarity between the structural elements from said subject and reference nucleic acid sequences, by comparing feature vectors produced from the extracted data from candidate secondary structures from said subject nucleic acid sequence with feature vectors produced from the extracted data from candidate secondary structures from said reference nucleic acid sequence,
    and wherein steps (a) and (b) are performed on a specifically programmed apparatus.

2. The method according to claim 1, wherein the structural element extracting step further comprises a step of dividing each candidate secondary structure into a stem structure and a marginal structure.

3. The method according to claim 2, wherein a feature vector is produced for each candidate secondary structure by producing and combining a feature vector for the stem structure and a feature vector for the marginal structure for each candidate secondary structure.

4. The method according to claim 1, wherein said structural element extracting step further comprises a step of numerically converting the extracted data for each structural element to obtain a feature vector for each candidate secondary structure.

5. The method according to claim 1, wherein said localized structural similarity evaluating step is performed by a correlational analysis of feature vectors obtained from said subject nucleic acid sequence with feature vectors obtained from said reference nucleic acid sequence.

6. The method according to claim 1, wherein said localized structural similarity evaluating step further comprises a step of obtaining a candidate score for feature vectors in the subject nucleic acid sequence.

7. The method according to claim 1, wherein said localized structural similarity evaluating step further comprises a step of obtaining a fixed score for feature vectors in the subject nucleic acid sequence.

8. The method according to claim 1, wherein the structural element extracting step further comprises the step of dividing structural units in the secondary structure candidate so as to extract a structural element from each of the structural units.

9. The method according to claim 8, wherein the structural element extracting step further comprises extracting a structural element for each stem structure and extracting a structural element for each marginal structure.

10. The method according to claim 1, wherein the structural element extracting step further comprises obtaining a feature vector for each structural element in said subject nucleic acid sequence and for each structural element in said reference nucleic acid sequence.

11. The method according to claim 1, wherein when the reference nucleic acid sequence has a plurality of feature vectors,
    in the localized structural similarity evaluating step,
    scores for feature vectors in the subject nucleic acid sequence relative to the respective feature vectors in the reference nucleic acid sequence are set as candidate scores.

12. The method according to claim 11, wherein,
    in the localized structural similarity evaluating step,
    among the candidate scores, a fixed score showing a similarity over a predetermined level is obtained.

13. The method according to claim 12, wherein,
    in the localized structural similarity evaluating step,
    based on the fixed score, a secondary structure within the subject nucleic acid sequence, having a high similarity to the reference nucleic acid sequence, is predicted.

14. The method according to claim 1, wherein
    when the subject nucleic acid sequence has a plurality of feature vectors,
    in the localized structural similarity evaluating step,
    scores for feature vectors in the subject nucleic acid sequence relative to the respective feature vectors in the reference nucleic acid sequence are set as candidate scores.

15. The method according to claim 1, wherein
    when the subject nucleic acid sequence has a plurality of candidate secondary structures,
    in the structural element extracting step,
    structural element data is extracted from each candidate secondary structure in said plurality of candidate secondary structures.

16. The method according to claim 1, wherein the structural element extracting step further comprises obtaining a candidate secondary structure from each of said subject and reference nucleic acid sequences.

17. An apparatus for predicting secondary structures within a nucleic acid, comprising:
    (a) an extractor unit for extracting data on structural elements of candidate secondary structures from a subject nucleic acid sequence and from a reference nucleic acid sequence; and
    (b) a localized structural similarity evaluator unit, for evaluating the structural similarity between the structural elements from said subject and reference nucleic acid sequences, by comparing feature vectors produced from the extracted data from candidate secondary structures from said subject nucleic acid sequence with feature vectors produced from the extracted data from candidate secondary structures from said reference nucleic acid sequence.

18. The apparatus according to claim 17, wherein said extractor divides each candidate secondary structure into a stem structure and a marginal structure.

19. The apparatus according to claim 18, wherein the extractor extracts a structural element for each stem structure and extracts a structural element for each marginal structure.

20. The apparatus according to claim 18, wherein a feature vector is produced for each candidate secondary structure by producing and combining a feature vector for the stem structure and a feature vector for the marginal structure for each candidate secondary structure.

21. The apparatus according to claim 17, wherein said extractor numerically converts the extracted data for each structural element to obtain a feature vector for each candidate secondary structure.

22. The apparatus according to claim 17, wherein said localized structural similarity evaluator performs a correlational analysis of feature vectors obtained from said subject nucleic acid sequence with feature vectors obtained from said reference nucleic acid sequence.

23. The apparatus according to claim 17, wherein said localized structural similarity evaluator obtains a candidate score for feature vectors in the subject nucleic acid sequence.

24. The apparatus according to claim 17, wherein said localized structural similarity evaluator obtains a fixed score for feature vectors in the subject nucleic acid sequence.

25. The apparatus according to claim 17, wherein the extractor divides structural units in the candidate secondary structure and extracts a structural element from each of the structural units.

26. The apparatus according to claim 17, wherein the extractor obtains a feature vector for each structural element in said subject nucleic acid sequence and for each structural element in said reference nucleic acid sequence.

27. The apparatus according to claim 17, wherein when the reference nucleic acid sequence has a plurality of feature vectors, the localized structural similarity evaluator sets scores for feature vectors in the subject nucleic acid sequence relative to the respective feature vectors in the reference nucleic acid sequence as candidate scores.

28. The apparatus according to claim 27, wherein among the candidate scores, the localized structural similarity evaluator obtains a fixed score showing a similarity over a predetermined level.

29. The apparatus according to claim 28, wherein based on the fixed score, the localized structural similarity evaluator predicts a secondary structure within the subject nucleic acid sequence having a high similarity to the reference nucleic acid sequence.

30. The apparatus according to claim 17, wherein when the subject nucleic acid sequence has a plurality of feature vectors, the localized structural similarity evaluator sets scores for feature vectors in the subject nucleic acid sequence relative to the respective feature vectors in the reference nucleic acid sequence as candidate scores.

31. The apparatus according to claim 17, wherein when the subject nucleic acid sequence has a plurality of candidate secondary structures, the extractor extracts structural element data from each candidate secondary structure in said plurality of candidate secondary structures.

32. The apparatus according to claim 17, wherein the extractor obtains a candidate secondary structure from each of said subject and reference nucleic acid sequences.

33. A non-transitory, computer-readable storage medium, storing a program for predicting secondary structures within a nucleic acid, said program executing the steps of:

(a) a structural element extracting step, comprising extracting data on structural elements of candidate secondary structures from a subject nucleic acid sequence and from a reference nucleic acid sequence;

(b) a localized structural similarity evaluating step, comprising evaluating the structural similarity between the structural elements from said subject and reference nucleic acid sequences, by comparing feature vectors produced from the extracted data from candidate secondary structures from said subject nucleic acid sequence with feature vectors produced from the extracted data from candidate secondary structures from said reference nucleic acid sequence.

* * * * *

```
SEQUENCE LISTING

<160> NUMBER OF SEQ ID NOS: 2

<210> SEQ ID NO 1
<211> LENGTH: 26
<212> TYPE: RNA
<213> ORGANISM: Artificial Sequence
<220> FEATURE:
<223> OTHER INFORMATION: example oligonucleotide containing secondary
      structure

<400> SEQUENCE: 1
aaacccgaaa ggguuuuuga gaaaaa                                          26

<210> SEQ ID NO 2
<211> LENGTH: 26
<212> TYPE: RNA
<213> ORGANISM: Artificial Sequence
<220> FEATURE:
<223> OTHER INFORMATION: example oligonucleotide containing secondary
      structure

<400> SEQUENCE: 2
cccccgagag ggguuuugcc cuugcc                                          26
```